United States Patent [19]

Hasspacher et al.

[11] 4,123,545

[45] * Oct. 31, 1978

[54] N-PROPYL-3(β-HYDROXYETHYL)-3-(META-HYDROXYPHENYL)-PYRROLIDINE

[75] Inventors: Klaus Hasspacher, Riehen; Michael Strasser, Binningen, both of Switzerland

[73] Assignee: Sandoz Ltd., Basel, Switzerland

[ * ] Notice: The portion of the term of this patent subsequent to Jun. 13, 1995, has been disclaimed.

[21] Appl. No.: 811,586

[22] Filed: Jun. 30, 1977

[51] Int. Cl.$^2$ .................... C07D 207/44; A61K 31/40
[52] U.S. Cl. .......................... 424/274; 260/326.5 M
[58] Field of Search ................. 260/326.5 M; 424/274

[56] References Cited

U.S. PATENT DOCUMENTS 3,745,171  7/1973  Lockhart .................. 260/326.5 M

*Primary Examiner*—Jose Tovar
*Attorney, Agent, or Firm*—Gerald D. Sharkin; Robert S. Honor; Timothy G. Rothwell

[57] ABSTRACT

The present invention provides a compound of the formula

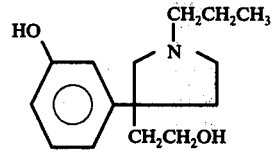

which possesses pharmacological activity, for example anti-psychotic activity.

3 Claims, No Drawings

N-PROPYL-3(β-HYDROXYETHYL)-3-(META-HYDROXYPHENYL)-PYRROLIDINE

The present invention provides the compound of formula I,

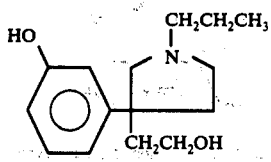

The invention further provides a process for the production of said compound comprising removing a protecting group R from a compound of formula II,

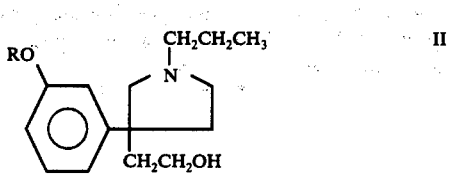

wherein R is a removable protecting group.

Suitable groups R for protecting the phenolic group and methods for their removal are known. Suitable protecting groups include aromatic radicals, for example benzyl or trityl, or lower aliphatic radicals, for example lower alkyl groups such as ethyl or, preferably, methyl or tetrahydropyranyl. The protecting group may be removed hydrolytically or hydrogenolytically in known manner, depending on the nature of the group. Hydrolytic removal of, e.g., alkyl groups may, for example, be effected in the presence of an acid, for example a Lewis acid, e.g. boron tribromide or aluminium chloride, at temperatures of between −80° to +70° C., or a strong mineral acid, e.g. hydrobromic acid or hydriodic acid, at temperatures of between about 20° and 150° C. The tetrahydropyranyl protecting group may, suitably, be removed under mildly acid conditions. Removal of the protecting group, e.g. the benzyl group, by hydrogenolysis may be effected, for example, in the presence of a catalyst, in a solvent which is inert under the reaction conditions, for example ethyl acetate or a lower alcohol, such as methanol or ethanol, at temperatures of between about 20° and 60° C. and at a hydrogen pressure of 1-200 atmospheres. Suitable catalysts are platinum, nickel or, preferably, palladium. The benzyl group may alternatively be removed by anionic debenzylation, e.g. with lithium halide in acetone.

The resulting compound of formula I may be isolated and purified using conventional techniques.

The free base form of the compound of formula I may be converted into salt forms, including acid addition salt forms, and vice versa in conventional manner.

The compounds of formula II may be produced in manner analogous to the processes described in the Example.

In the following non-limitative Example, all temperatures are in degrees Celsius.

EXAMPLE:
3-m-Hydroxyphenyl-1-propyl-3-pyrrolidine ethanol 26.8 g of 3-m-Benzyloxyphenyl-1-propyl-3-pyrrolidine ethanol are dissolved in 400 ml of ethanol, 2.5 g of palladium (10% on charcoal) are added and hydrogenation is effected for 20 hours at 35° under a hydrogen pressure of 5 atmospheres. After take-up of 2 liters of hydrogen, the catalyst mixture is filtered off and the reaction mixture reduced in volume using a rotary evaporator. The resulting yellow oil (20 g) is taken up in methanol (50 ml) and a solution of 11.4 g of naphthalene disulphonic acid in 50 ml of methanol is added. The title compound, in the form of the 1,5-naphthalene disulphonate, crystallises out. M.P. 201°–202°.

The starting material can be obtained as follows:

(a) 20 g of 3-m-Methoxyphenyl-5-oxo-3-pyrrolidine acetic acid are dissolved in 100 ml of glacial acetic acid and 20 g of 63% hydrobromic acid, and boiled at reflux for 7 hours. The clear yellow reaction solution is evaporated and then 100 ml of water are added. The 3-m-hydroxyphenyl-5-oxo-3-pyrrolidine acetic acid crystallizes. M.P. 193°–195°.

(b) 20 g of 3-m-Hydroxyphenyl-5-oxo-pyrrolidine acetic acid are dissolved in 200 ml of ethanol, and then 6.8 g of sodium hydroxide are added. A solution of 29.1 g of benzyl bromide in 200 ml of ethanol is added in drops at room temperature over the course of 20 minutes to the suspension formed, whereupon the reaction solution becomes clear. The solution is further stirred at room temperature for 2½ hours. The crystallisate formed is filtered off, washed with a little ethanol/ether (5:95%) and dried. M.P. of the 3-m-benzyloxyphenyl-5-oxo-3-pyrrolidine acetic acid: 260°–265°.

(c) 3-m-Benzyloxyphenyl-3-pyrrolidine ethanol is produced by the reduction of 25 g of 3-m-benzyloxyphenyl-5-oxo-3-pyrrolidine acetic acid with 5.85 g of lithium aluminium hydride in 500 ml of anhydrous tetrahydrofuran over a period of 20 hours at reflux temperature. After decomposing the excess reducing agent with water/tetrahydrofuran (1:1) in the cold, the liquid is filtered from the resultant hydroxide sediment, which is boiled out twice, each time with 200 ml of tetrahydrofuran. The combined clear tetrahydrofuran solutions are evaporated to dryness, the pH of the solution adjusted to 3 and the residue taken up in a little ethanol and hydrochloric acid. The hydrochloride form of the title compound is crystallized. M.P. 163°–168°.

(d) 40 g of 3-m-Benzyloxyphenyl-3-pyrrolidine, in the presence of 9.4 g of propionaldehyde and 0.5 g of platinum oxide in 650 ml of ethanol, are hydrogenated at 50°/5 atm for 18 hours. After take-up of the hydrogen is complete, the catalyst is filtered off and the filtrate evaporated. The 3-m-benzyloxyphenyl-1-propyl-3-pyrrolidine ethanol is obtained as a yellow oil and used for the next step witout further purification.

The compound of formula I is useful because it possesses pharmacological activity in animals. In particular, the compound is useful in the treatment of pyschotic disturbances such as schizophrenia, as indicated by its activity in standard tests, e.g. in the morphine antagonism test in mice on i.p. administration of from 10 to 40 mg/kg animal body weight and on i.v. administration of 18 mg/kg animal body weight; on i.v. administration of 18 mg/kg animal body weight in rats and on i.v. administration of 18 mg/kg animal body weight to rhesus monkeys.

For this use, the dosage will, of course, vary depending on the mode of administration and treatment desired. However, in general, satisfactory results are obtained when administered at a daily dosage of from 0.5 to 40 mg/kg animal body weight, conveniently given in divided doses 2 to 4 times a day or in sustained release form. For the larger animals, the total daily dosage is in the range of from 30 to 300 mg, and dosage forms suitable for oral administation comprise from 7 to 150 mg of the compound admixed with a solid or liquid pharmaceutical carrier or diluent.

The compound may be administered in pharmaceutically acceptable salt form, including phenolates and acid addition salt forms. Such salt forms exhibit the same order of activity as the free base form and are readily prepared in conventional manner. Representative acids for acid addition salt forms include organic acids such as naphthalene-1,5-disulphonic acid and maleic acid and mineral acids such as hydrochloric acid. Suitable bases for phenolate formation include alkali metal hydroxides. The present invention also provides a pharmaceutical composition comprising a compound of formula I, in free base form or in pharmaceutically acceptable salt form, in association with a pharmaceutically acceptable carrier or diluent. Such compositions may be in the form of, for example, a solution or a capsule.

What is claimed is:

1. A compound of the formula

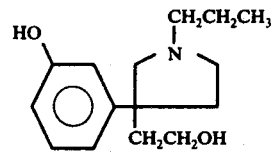

or a pharmaceutically acceptable salt form thereof.

2. A method of treating psychotic disturbances in animals which comprises administering to an animal in need of such treatment a therapeutically effective amount of a compound of claim 1.

3. A pharmaceutical composition comprising a compound of claim 1 in association with a pharmaceutically acceptable carrier or diluent.